US012702564B2

(12) United States Patent
Ek et al.

(10) Patent No.: US 12,702,564 B2
(45) Date of Patent: Aug. 11, 2026

(54) SYSTEM AND METHOD FOR REPAIRING ARTICULAR SURFACES

(71) Applicant: Arthrosurface Incorporated, Franklin, MA (US)

(72) Inventors: Steven W. Ek, Durham, NH (US); Steven E. Ek, Bolton, MA (US); Nikhil T. Jawrani, Framingham, MA (US)

(73) Assignee: Arthrosurface Incorporated, West Bridgewater, MA (US)

( * ) Notice: Subject to any disclaimer, the term of this patent is extended or adjusted under 35 U.S.C. 154(b) by 610 days.

(21) Appl. No.: 18/165,871

(22) Filed: Feb. 7, 2023

(65) Prior Publication Data

US 2023/0255780 A1 Aug. 17, 2023

Related U.S. Application Data

(63) Continuation of application No. 16/854,270, filed on Apr. 21, 2020, now Pat. No. 11,766,334, which is a (Continued)

(51) Int. Cl.
*A61F 2/46* (2006.01)
*A61B 17/064* (2006.01)
(Continued)

(52) U.S. Cl.
CPC ............ *A61F 2/40* (2013.01); *A61B 17/0642* (2013.01); *A61F 2/28* (2013.01); *A61F 2/30* (2013.01);
(Continued)

(58) Field of Classification Search
CPC ...... A61F 2/40; A61F 2/28; A61F 2/30; A61F 2/30756; A61F 2/4081; A61F 2/4606; A61F 2/4618; A61F 2/4637; A61F 2002/305; A61F 2002/30649; A61F 2002/3085; A61F 2002/4627; A61F 2002/4628; A61B 2017/0409; A61B 2017/044; A61B 2017/0648; A61B 17/0642
(Continued)

(56) References Cited

U.S. PATENT DOCUMENTS 5,100,417 A * 3/1992 Cerier ................ A61B 17/0401 606/232
5,152,790 A * 10/1992 Rosenberg ............ A61F 2/0811 606/328

(Continued)

*Primary Examiner* — Jessica Weiss
(74) *Attorney, Agent, or Firm* — Secant IP, P.L.L.C.

(57) ABSTRACT

A total joint replacement system comprising a first and a second implant system. The first implant system includes a first implant having a first load bearing surface based on a first removed portion of an articular surface of a patient's first bone, and a first anchor having a first threaded region configured to be secured into the first bone, wherein the first anchor is configured to be secured to the first implant. The second implant system includes a second implant having a second load bearing surface based on a second removed portion of an articular surface of a patient's second bone, and a second anchor having a second threaded region configured to be secured into the second bone, wherein the second anchor is configured to be secured to the second implant.

20 Claims, 17 Drawing Sheets

Related U.S. Application Data continuation of application No. 15/973,981, filed on May 8, 2018, now Pat. No. 10,624,754, which is a continuation of application No. 14/640,774, filed on Mar. 6, 2015, now Pat. No. 9,962,265.

(60) Provisional application No. 61/950,762, filed on Mar. 10, 2014, provisional application No. 61/949,824, filed on Mar. 7, 2014, provisional application No. 61/949,789, filed on Mar. 7, 2014, provisional application No. 61/949,774, filed on Mar. 7, 2014.

(51) Int. Cl.

| | |
|---|---|
| ***A61F 2/28*** | (2006.01) |
| ***A61F 2/30*** | (2006.01) |
| ***A61F 2/40*** | (2006.01) |
| *A61B 17/04* | (2006.01) |

(52) U.S. Cl.

CPC ........ *A61F 2/30756* (2013.01); *A61F 2/4081* (2013.01); *A61F 2/4606* (2013.01); *A61F 2/4618* (2013.01); *A61F 2/4637* (2013.01); *A61B 2017/0409* (2013.01); *A61B 2017/044* (2013.01); *A61B 2017/0648* (2013.01); *A61F 2002/30331* (2013.01); *A61F 2002/30364* (2013.01); *A61F 2002/30405* (2013.01); *A61F 2002/30462* (2013.01); *A61F 2002/305* (2013.01); *A61F 2002/30649* (2013.01); *A61F 2002/3085* (2013.01); *A61F 2002/4627* (2013.01); *A61F 2002/4628* (2013.01); *A61F 2310/00011* (2013.01)

(58) Field of Classification Search

USPC ........................................................... 606/99

See application file for complete search history.

(56) References Cited

U.S. PATENT DOCUMENTS

| | | | | | |
|---|---|---|---|---|---|
| 5,258,016 | A * | 11/1993 | DiPoto | A61B 90/06 | 606/232 |
| 5,993,459 | A * | 11/1999 | Larsen | A61B 17/0469 | 606/104 |
| 9,023,088 | B2 * | 5/2015 | Voisard | A61B 17/0642 | 606/313 |
| 2002/0055783 | A1 * | 5/2002 | Tallarida | A61B 17/1764 | 623/20.14 |
| 2010/0211120 | A1 * | 8/2010 | Bonutti | A61B 17/8685 | 606/86 R |
| 2011/0230965 | A1 * | 9/2011 | Schell | A61F 2/4611 | 606/86 A |

* cited by examiner

SYSTEM AND METHOD FOR REPAIRING ARTICULAR SURFACES

CROSS-REFERENCE TO RELATED APPLICATIONS

This application is a continuation U.S. patent application Ser. No. 16/854,270, filed Apr. 21, 2020, which is a continuation of U.S. patent application Ser. No. 15/973,981 (now U.S. Pat. No. 10,624,754), filed May 8, 2018, which is a continuation of U.S. patent application Ser. No. 14/640,774 (now U.S. Pat. No. 9,962,265), filed Mar. 6, 2015, which claims the benefit of U.S. Provisional Application Ser. No. 61/949,774, filed Mar. 7, 2014; U.S. Provisional Application Ser. No. 61/949,789, filed Mar. 7, 2014; U.S. Provisional Application Ser. No. 61/949,824, filed Mar. 7, 2014; and U.S. Provisional Application Ser. No. 61/950,762, filed Mar. 10, 2014, the entire disclosures of which are fully incorporated herein by reference.

FIELD

The present disclosure relates to delivery systems for bone implants, and more particularly, to delivery systems for articular surface implants.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. One method of installing an implant involves applying a blunt force, e.g. a hammer/mallet or the like, to the implant. Unfortunately, some of the blunt force is transmitted from the implant into the surrounding bone and/or tissue and can cause damage to the bone/tissue. This is particularly problematic in small bones (such as, but not limited to, bones in the hand and/or foot) as well as patients who suffer from reduced bone mass and density that can lead to fracture (such as, but not limited to osteoporosis or the like).

BRIEF DESCRIPTION OF THE DRAWINGS

Features and advantages of the claimed subject matter will be apparent from the following detailed description of some example embodiments consistent therewith, which description should be considered with reference to the accompanying drawings, wherein:

DETAILED DESCRIPTION

Figures 1, 2, 3:
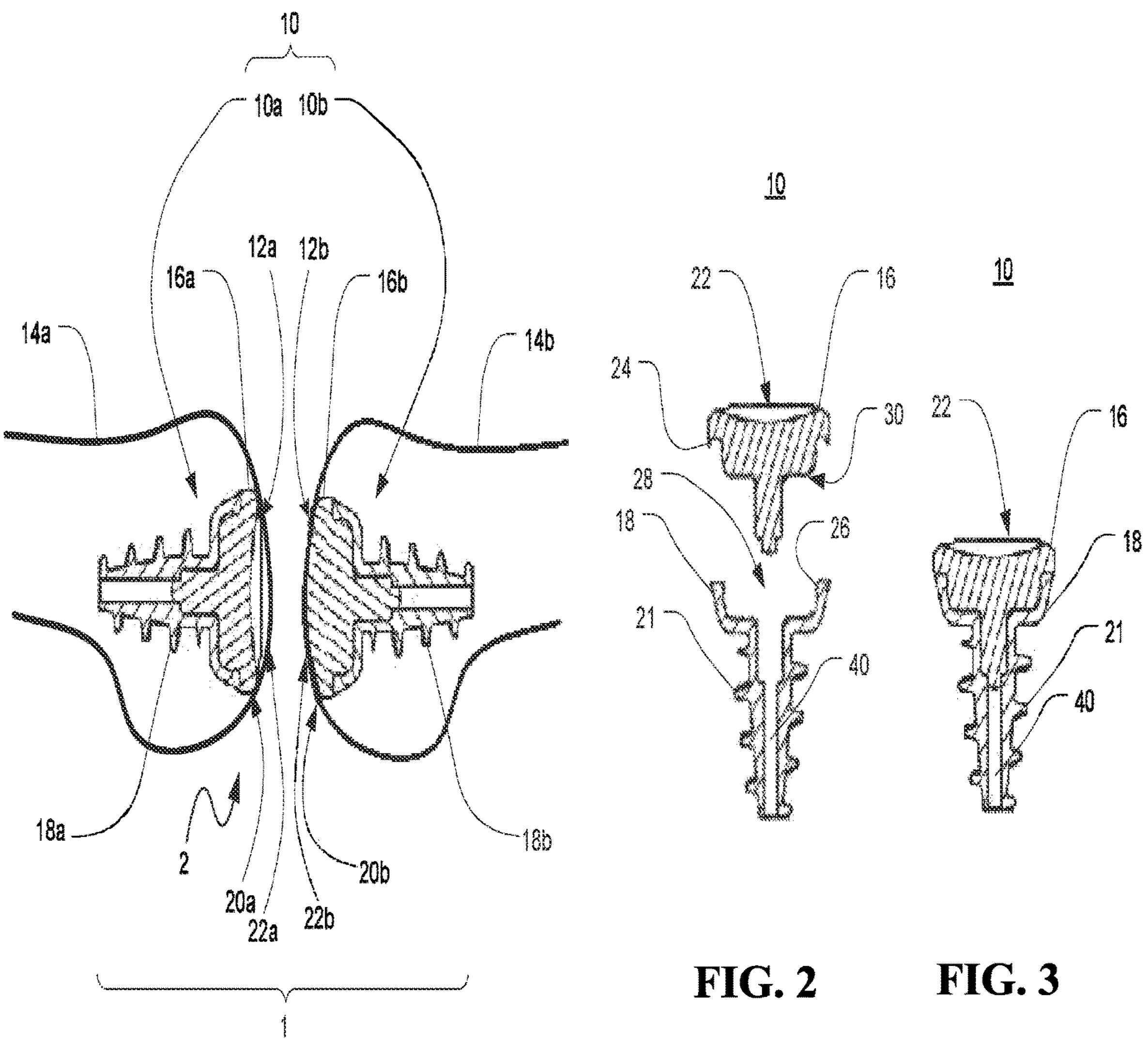
FIG. 1 generally illustrates a total joint replacement system installed in a patient's joint consistent with at least one embodiment of the present disclosure.
FIGS. 2 and 3 generally illustrate one embodiment of an implant system which may be used with the total joint replacement system consistent with at least one embodiment of the present disclosure.

With reference to FIG. 1, one embodiment of total joint replacement system 1 installed in a patient's joint 2 is generally illustrated. The total joint replacement system 1 may include two or more implant system is 10 (e.g., a first and a second implant system 10*a*, 10*b*) installed in the articular surface 12*a*, 12*b* of a patient's bone 14*a*, 14*b*, respectively. Each one of the implant systems 10 is configured to repair and/or replace the articular surface 12*a* and/or 12*b* (referred to as articular surface 12 for simplicity) of a respective one of the patient's bones 14*a* and/or 14*b* (referred to as bone 14 for simplicity). The total joint replacement system 1 may be used with implant systems 10 for replacing any articular surface 12 such as, but not limited to, shoulder joints (e.g., but not limited to, the glenohumeral joint), hip joints (e.g., but not limited to, the acetabulofemoral joint), foot and/or hand joints (e.g., but not limited to, metacarpophalangeal joints, metatarsophalangeal joints, and/or interphalangeal joints), knee joints, elbow joints, or the like. One or more of the implant systems 10 may include total joint implants (wherein all or substantially all of the articular surface of at least one bone is replaced with the artificial surface of the implant) and/or partial implants (wherein substantially only the damaged portion(s) of the articular surface 12 of a bone 14 is replaced with the artificial surface of the implant). As explained herein, the implant systems 10*a*, 10*b* as illustrated in FIG. 1 are for illustrative purposes only, and the total joint replacement system 1 may be used with any implant system 10 as described herein.

Turning now to FIGS. 2-3, one embodiment of an implant system 10 which may be used with the total joint replacement system 1 consistent with the present disclosure is generally illustrated. For example. FIG. 2 generally illustrates one embodiment of an exploded, unassembled implant system 10, and FIG. 3 generally illustrates an assembled implant system 10. The implant system 10 may generally include an implant (e.g., implant body) 16 configured to be secured to an anchor 18. The anchor 18 is configured to be secured to the bone 14 within an excision site 20 formed beneath the patient's articular surface 12 such that a load bearing surface 22 of the implant 16 is generally flush with the patient's surrounding articular surface 12 as generally illustrated in FIG. 1.

The load bearing surface 22 may have any surface contour depending on the intended application. The load bearing surface 22 may be based on or generally correspond to the original contour of the patient's removed articular surface. For example, the load bearing surface 22 may have a contour substantially corresponding to or based on the contour of an articular surface of a patient being repaired. The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior curvature and the superior inferior curvature. One or more of the anterior-posterior and/or superior-inferior curvatures may themselves be based on multiple curves, (for example, as generally described in U.S. patent application Ser. No. 12/027,121, filed Feb. 6, 2008 and entitled System and Method for Joint Resurface Repair, which is fully incorporated herein by reference).

While the load bearing surface 22 in FIGS. 2 and 3 is illustrated having a generally convex contour, it should be appreciated that the load bearing surface 22 is not limited to this configuration and will depend on the intend application. For example, the load bearing surface 22 may include, but is not limited to, generally concave configurations (e.g., as generally illustrated in FIG. 1) and/or generally hemi-spherical shapes.

The excision site 20 may be formed using any method and system known to those skilled in the art, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. According to one embodiment, the anchor 18 may be secured to the bone 14, for example, using one or more external threads, ribs, protrusions, bone cement, barbs, grooves or any other structure 21 that enables the anchor 18 to be secured to the bone 14. The use of threads 21 as generally illustrated may advantageously allow the height of the implant 12 to be adjusted by rotating the anchor 18 within the bone 14 such that the implant 16 is flush with the surrounding articular surface 12.

The anchor 18 is configured to engage and/or secure the implant assembly 10 to the patient's bone as described herein. Anchor 18 includes a proximal and a distal end region, and optionally may include a cannulated passageway 40. The cannulated passageway 40 may be configured to be advanced over a guide wire (not shown) extending outwardly from the excision site in the bone as generally described in U.S. Pat. Nos. 6,520,964, 6,610,067, 6,679,917, and 7,678,151, all of which are fully incorporated herein by reference. The use of a cannulated passageway 40 and the guide wire may facilitate alignment of the anchor 30 with respect to the excision site and the surrounding articular surface.

As discussed above, the implant 16 may be secured to the anchor 18 by way of a connection. For example, the implant 16 may include at least one first fixation element 24 configured to engage with at least one second fixation element 26 of the anchor 18 to secure the implant 16 to the anchor 18. According to one embodiment, the first and the second fixation elements 24, 26 may include one or more recesses, groves, slots or the like configured to corresponding to one or more protrusions, ribs, barbs, or the like, for example, in a snap-fit arrangement in which the first and/or second fixation elements resiliently deflect. The first and second fixation elements 24, 26 may be disposed about the entire perimeter/periphery of the implant 16 and anchor 18, and/or about one or more regions of the perimeter/periphery. The first and second fixation elements 24, 26 may prevent the implant 16 from becoming free relative to the anchor 18 (for example, to prevent axial and/or rotational movement of the implant 16 relative to the anchor 18). Optionally, the implant 16 may be at least partially received in an implant cavity 28 formed in the anchor 18 such that a bone facing surface 30 of the implant 16 engages against at least a portion of the implant cavity 28, thereby preventing the implant 16 from moving distally when a force is applied to the load bearing surface 22.

It should be appreciated that while the first and second fixation elements 24, 26 are generally illustrated as a recess and a protrusion, respectively, the implant system 10 consistent with the present disclosure is not limited to this arrangement unless specifically claimed as such. For example, the first and second fixation elements 24, 26 may include a protrusion and a recess, respectively, as well as other embodiments. Additionally, the anchor 18 may optionally include a passageway 40, for example, a longitudinal passageway, configured to be advanced over a guide wire (not shown) as generally described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. For example, the anchor 18 may be inserted into bone 14 or may be inserted into a shaft drilled in the bone 14 to reduce risks or complications arising from the insertion of the anchor 18. Without limitation, a pilot hole may be formed in the bone 14 for receiving the anchor 18 prior to installing the anchor 18. A diameter of the pilot bole may be smaller than the anchor 18, although example embodiments may vary and are not limited thereto.

Figure 4:
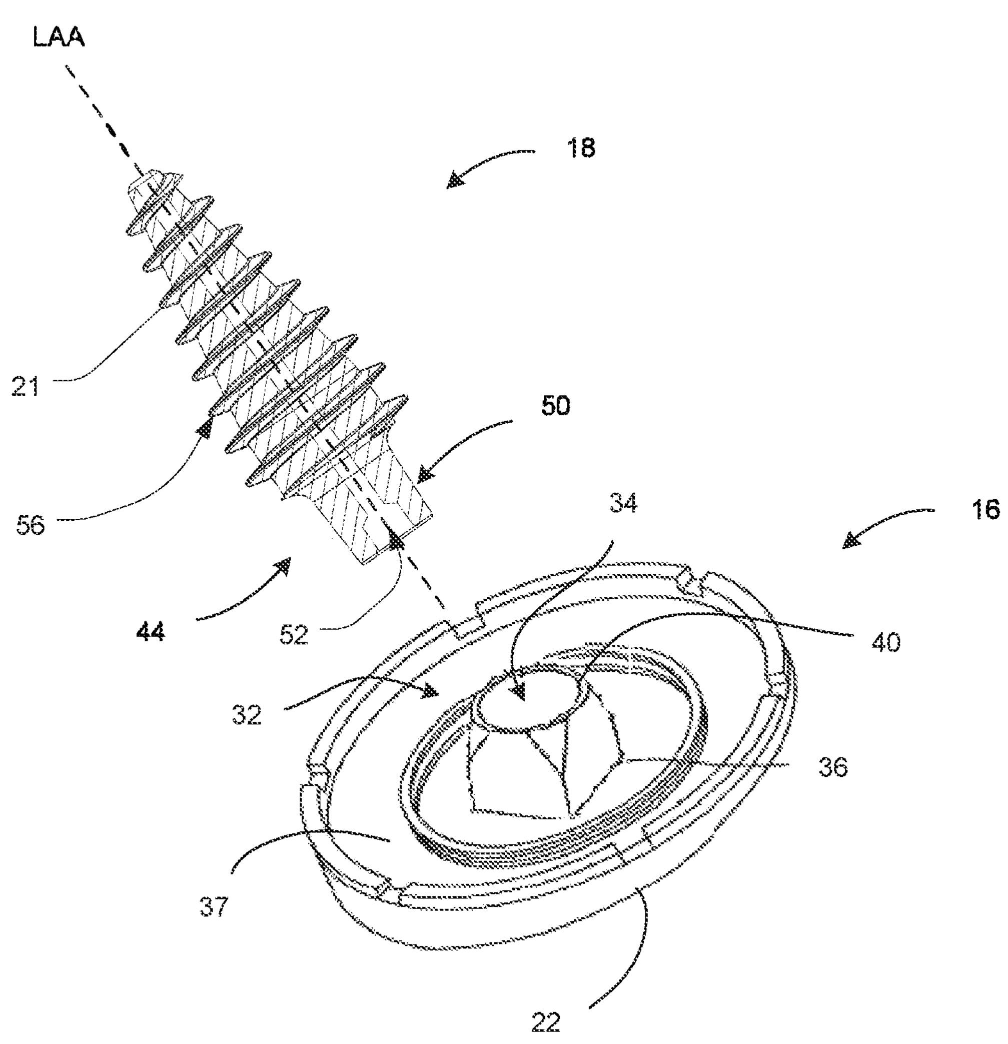
FIG. 4 generally illustrates another embodiment of an implant system which may be used with the total joint replacement system consistent with at least one embodiment of the present disclosure.

Turning now to FIG. 4, another embodiment of an implant system 10 which may be used with the total joint replacement system 1 consistent with the present disclosure is generally illustrated. Implant system 10 includes an implant (e.g., implant body) 16 configured to be secured to an anchor 18. Implant 16 may be formed of a plastic composition and may more particularly comprise, essentially consist of, or consist of a plastic composition. Exemplary plastic compositions may comprise thermoplastic compositions such as polyether ether ketone (PEEK) and polyethylene (PE), including ultrahigh molecular weight polyethylene (UHMWPE) and high density polyethylene (HDPE). In other embodiments, implant 16 may be formed of a metal composition and may more particularly comprise, essentially consist of, or consist of a metal composition. Exemplary metal compositions may comprise stainless steel, titanium, aluminum, chromium cobalt, and/or any alloy thereof.

Implant 16 has a joint facing side including a load bearing (joint articulation) surface 22 having any contour as described herein, and a bone facing surface 37. Bone facing surface 37 may substantially correspond to a contour of an excision site 20 (FIG. 1) formed in an articular surface 12 of a patient. More particularly, a perimeter of the implant 20 may substantially corresponds to a perimeter of an excision site 20 formed in the articular surface 12.

Bone facing surface 37 includes a first fixation element 32. First fixation element 32 comprises a fixation recess 34 formed in a fixation base 36 of implant 16. As shown, fixation recess 34 is substantially cylindrical and may be centered around a longitudinal axis LAA of the anchor 18. More particularly, the sidewall 40 of fixation recess 34 is tapered.

The anchor 18 is configured to engage and/or secure the implant assembly 10 to the patient's bone as described herein, for example, using threads 21 and/or bone cement. The proximal end region of the anchor 18 includes a second fixation element 44 configured to form a connection with the first fixation element 32. As shown by the figures, anchor 18 may comprise a screw with a fully or partially threaded tapered or non-tapered cylindrical shank which is arranged substantially transverse to the overlying portion of the load bearing surface 22.

As discussed herein, second fixation element 44 is configured to engage with the first fixation element 32 to form a connection therebetween. In the illustrated embodiment, the second fixation element 44 includes a tapered (male) protrusion. The tapered protrusion includes a tapered sidewall 50 configured to contact and abut against at least a portion of a tapered sidewall 40 of the first fixation element 32 to form a frictional connection therebetween. Of course, it should be appreciated that the arrangement of the male and female tapers with respect to the first and second fixation elements 32, 44 may be switched (e.g., the first fixation element 32 may include a male taper and the second fixation element 44 may include a female taper).

The proximal end region of the anchor 30 may also include a driver receptacle 52 arranged to receive a drive member therein, particularly to drive the first anchor 30 into bone. For example, driver receptacle 52 may be arranged to receive a drive member (not shown) to cause one or more anchor elements 56 of the anchor 18 to engage the bone 14. The driver receptacle 52 may allow torque to be transmitted to the anchor 18 to rotate the anchor 18 such that one or more external screw (helical) threads 21 threadably engage and connect with the bone 14.

Elongated anchor 18 may be formed of a plastic composition and may more particularly comprise, essentially consist of, or consist of a plastic composition. Exemplary plastic compositions may comprise thermoplastic compositions such as polyether ether ketone (PEEK) and polyethylene (PE) such as ultrahigh molecular weight polyethylene (UHMWPE) and high density polyethylene (HDPE). In other embodiments, anchor 18 may be formed of a metal composition and may more particularly comprise, essentially consist of, or consist of a metal composition. Exemplary metal compositions may comprise stainless steel, titanium, aluminum, chromium cobalt, and/or any alloy thereof.

Figure 5:
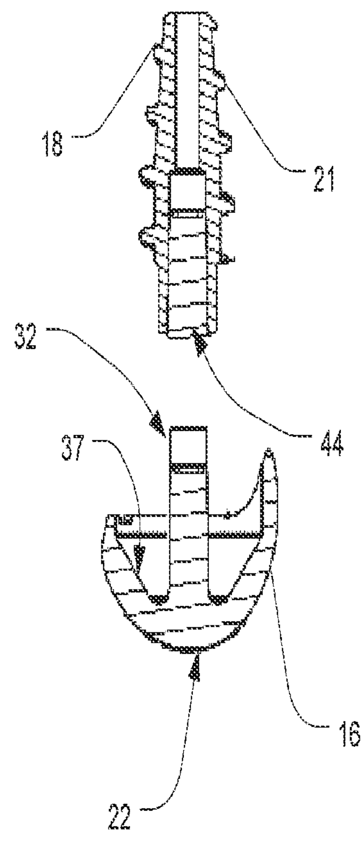
FIGS. 5 and 6 generally illustrate a further embodiment of an implant system which may be used with the total joint replacement system consistent with at least one embodiment of the present disclosure.
Figure 6:
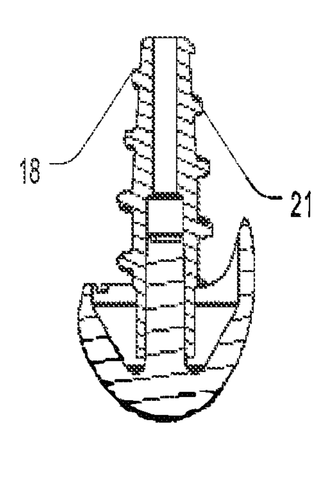
Figures 7A, 7B, 7C, 7D, 7E:
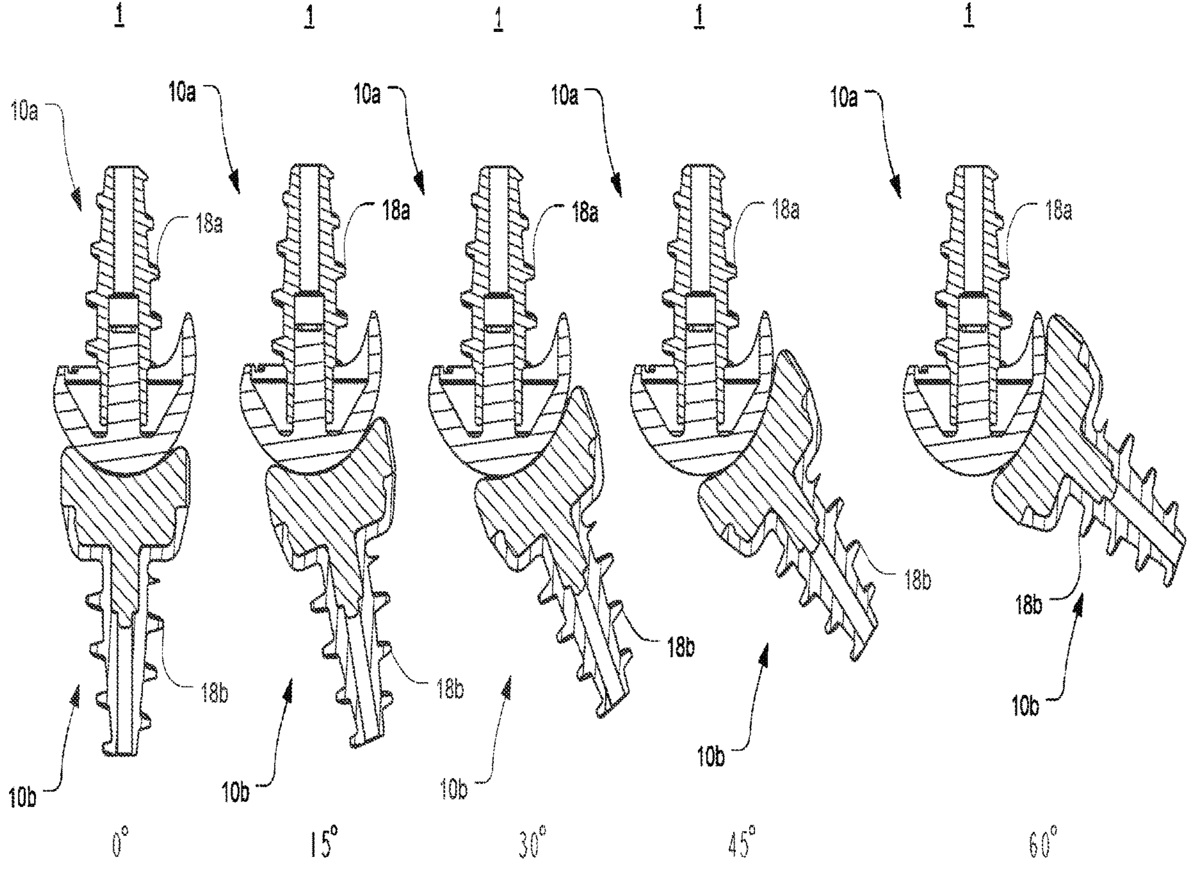
FIGS. 7*a*-7*e* generally illustrate cross-sectional views of another embodiment of the total joint replacement system consistent with at least one embodiment of the present disclosure at different angles.

Turning now to FIGS. 5-6, yet another embodiment of an implant system 10 which may be used with the total joint replacement system 1 consistent with the present disclosure is generally illustrated. For example, FIG. 5 generally illustrates one embodiment of an exploded, unassembled implant system 10, and FIG. 6 generally illustrates an assembled implant system 10. Implant 16 has a load bearing surface 22 and a bone facing surface 37. The load bearing surface 22 may have contour as described herein, for example, the original contour of the patient's articular surface generally corresponding to a plurality of overlapping excision sites (e.g., if replacing the dorsal socket or the like). The bone facing surface 37 may also include a first fixation element 32 configured to be secured to a second fixation element 44 of the anchor 18 to form a connection therebetween. In the illustrated embodiment, the first fixation element 32 includes a tapered (male) protrusion and the second fixation element 44 includes a tapered recess. The tapered protrusion includes a tapered sidewall configured to contact and abut against at least a portion of a tapered sidewall of the tapered recess to form a frictional connection therebetween. Of course, if should be appreciated that the arrangement of the male and female tapers with respect to the first and second fixation elements 32, 44 may be switched (e.g., the first fixation element 32 may include a female taper and the second fixation element 44 may include a male taper).

FIGS. 7*a*-7*e* generally illustrate cross-sectional views of another embodiment of the total joint replacement system 1 consistent with the present disclosure at different angles, e.g., ranging between 0° and 60°. The total joint replacement system 1 includes a first implant system 10*a* as generally described herein with respect to FIGS. 5 and 6, and a second implant system 10*b* as generally described herein with respect to FIGS. 2 and 3. For the sake of clarity, the bones of the joint are not illustrated.

The anchors 18*a* of the first implant system 10*a* may be secured to bone as described herein. For example, the height of the anchor 18*a* may be adjusted by rotating the anchor 18*a*. Optionally, a trial guide (not shown) may be coupled to the anchor 18*a* to allow the surgeon to verify that the load bearing surface 22 is substantially flush with the surrounding articular surface (if present) and/or generally corresponds to the location of the original articular surface.

The anchor 18*b* of the second implant system 10*b* may also be secured to the bone as described herein. Similarly, the height the anchor 18*b* may be adjusted by rotating the anchor 18*b*, and optionally using an implant trial guide (not shown). One advantage of the total joint replacement system 1 is that the height of the anchors 18*a*, 18*b* may be infinitely adjusted, and once adjusted to the desired height, the implant 16*a*, 16*b* may be secured to the anchors 18*a*, 18*b* in the correct orientation. For example, the implant 16*a* (because it has a non-symmetrical load bearing surface 22) should be aligned in a predetermined orientation with respect to the bone (e.g., the metatarsal bone). Similarly, the implant 16*b* should be aligned in a predetermined orientation with respect to the phalangeal bone and/or the first implant 16*a* (e.g., the implant 16*b* may have a generally convex contour configured to generally align with and slide against the implant 16*a* as generally illustrated in FIGS. 7*a*-7*e*). Thus, the height and/or separation distance between the bones (e.g., metatarsal and phalangeal bones) may be infinitely adjusted without impacting the alignment of the implants

16*a*, 16*b* (i.e., the alignment of the implants 16*a*, 16*b* may be independent of the position of the anchors 18*a*, 18*b*).

Figure 8:
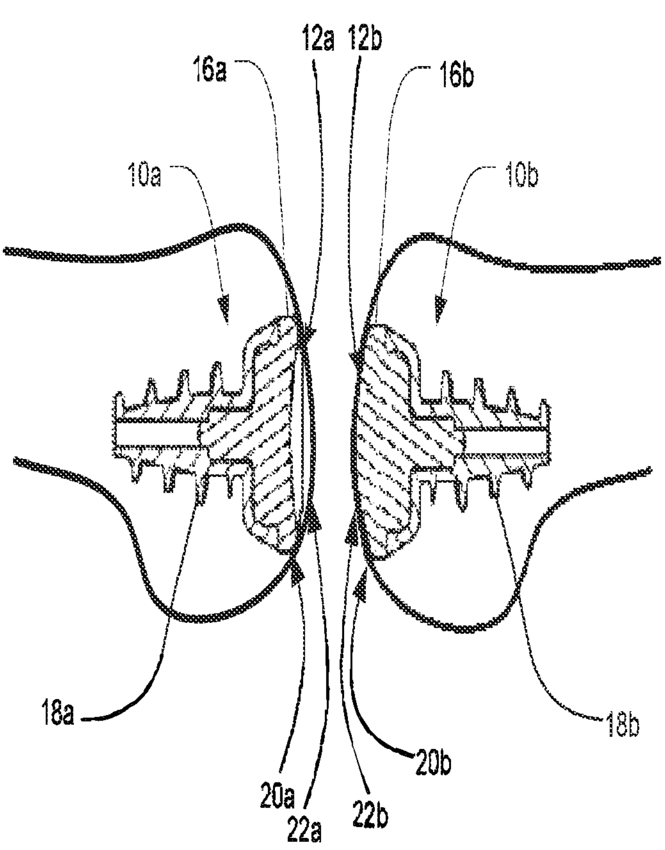
FIG. 8 generally illustrates a further embodiment of an implant system which may be used with the total joint replacement system consistent with at least one embodiment of the present disclosure.

Turning now to FIG. 8, yet another embodiment of the total joint replacement system 1 is generally illustrated. The total joint replacement system 1 includes a first and second implant system 10*a*, 10*b* similar to the implant systems 10 as generally described herein with respect to FIGS. 2 and 3. In particular, the first implant system 10*a* includes an implant 16*a* having a generally convex load bearing surface 22*a* and the second implant system 10*b* includes an implant 166 having a generally concaved load bearing surface 22*b* configured to mate with load bearing surface 22*a*.

Turning now to FIGS. 9-17, systems and methods for securing an anchor 18 into the bone and securing the implant 16 to the anchor 18 using an implant delivery system 100 consistent with the present disclosure are generally illustrated. In a first mode (as generally illustrated in FIGS. 9-13), the implant delivery system 100 may be used to secure the anchor 18 into an excision site formed in the bone. In a second mode (FIGS. 14-17), the delivery system 100 may be used to secure the implant 16 to the anchor 18 to assemble the implant system 10 within the excision site. As may be appreciated, the implant delivery system 100 may be used with any implant system 10 described herein and is not limited to the illustrated implant system 10 unless specifically claimed as such.

Figure 10:
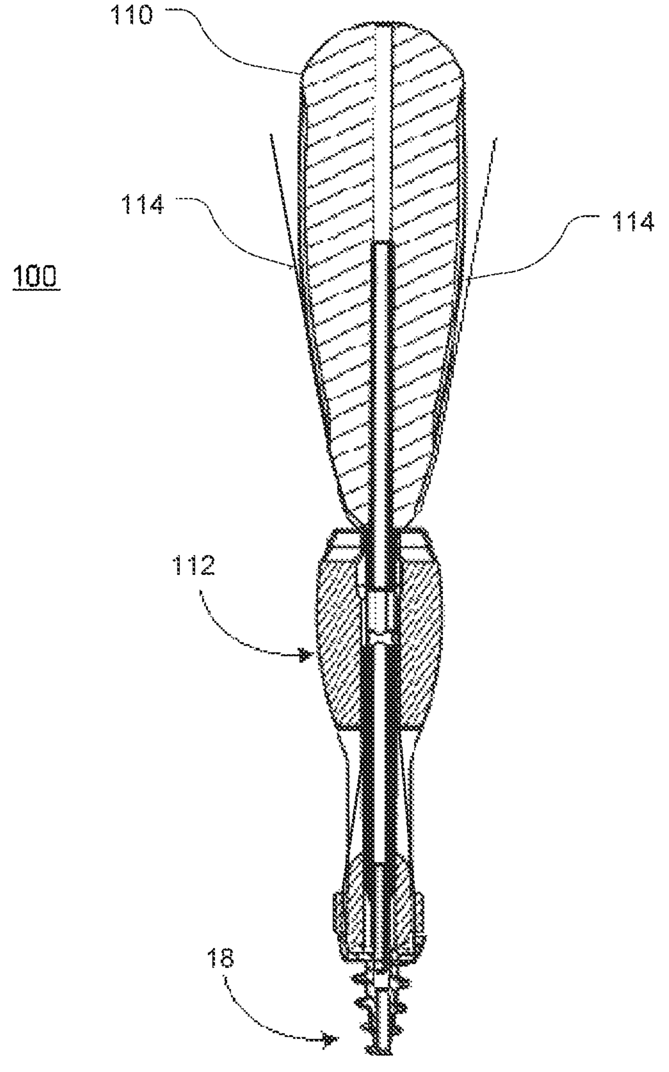
FIGS. 10-12 generally illustrate various steps in the installation of an anchor consistent with at least one embodiment of the present disclosure.
Figure 11:
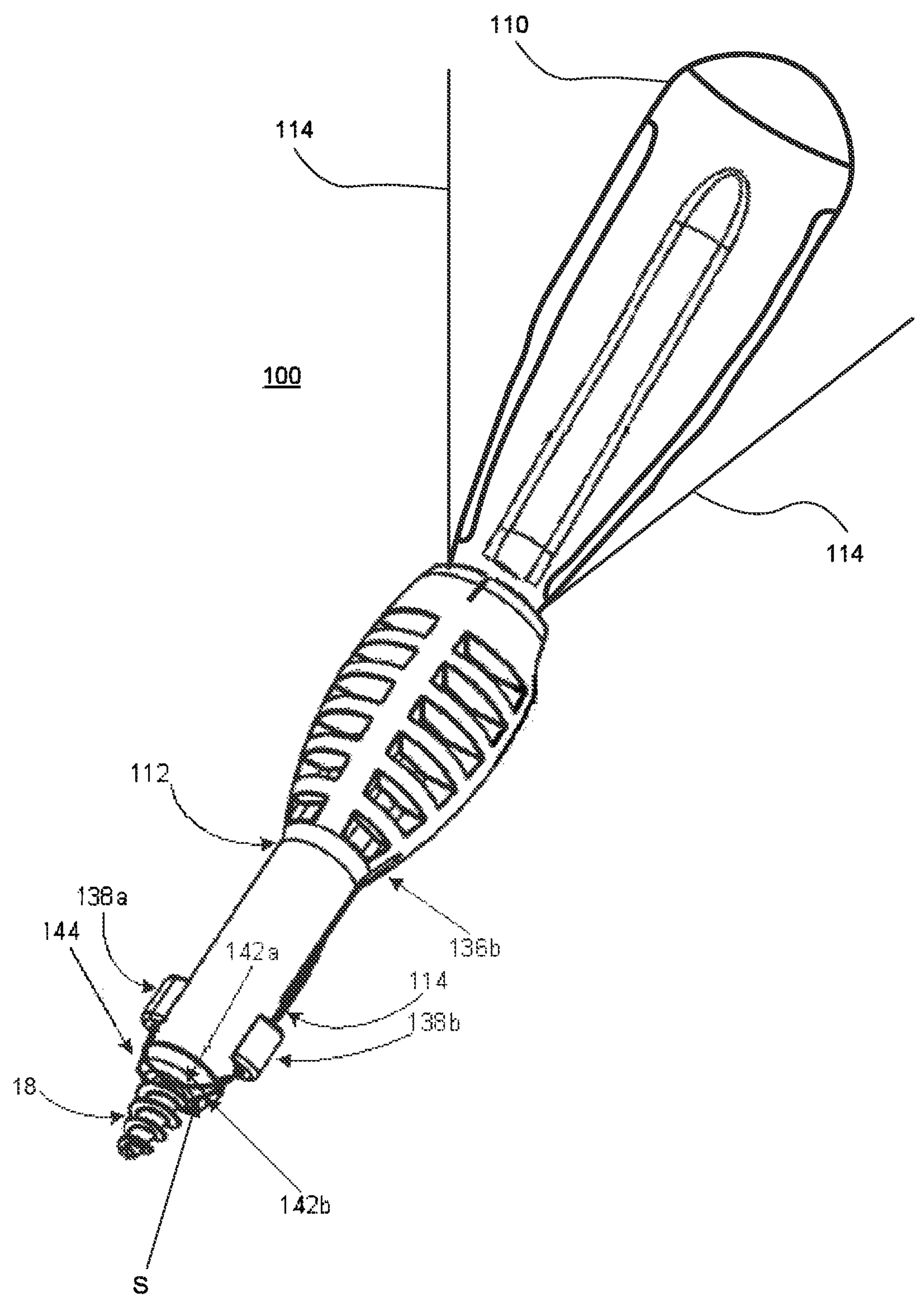
Figure 12:
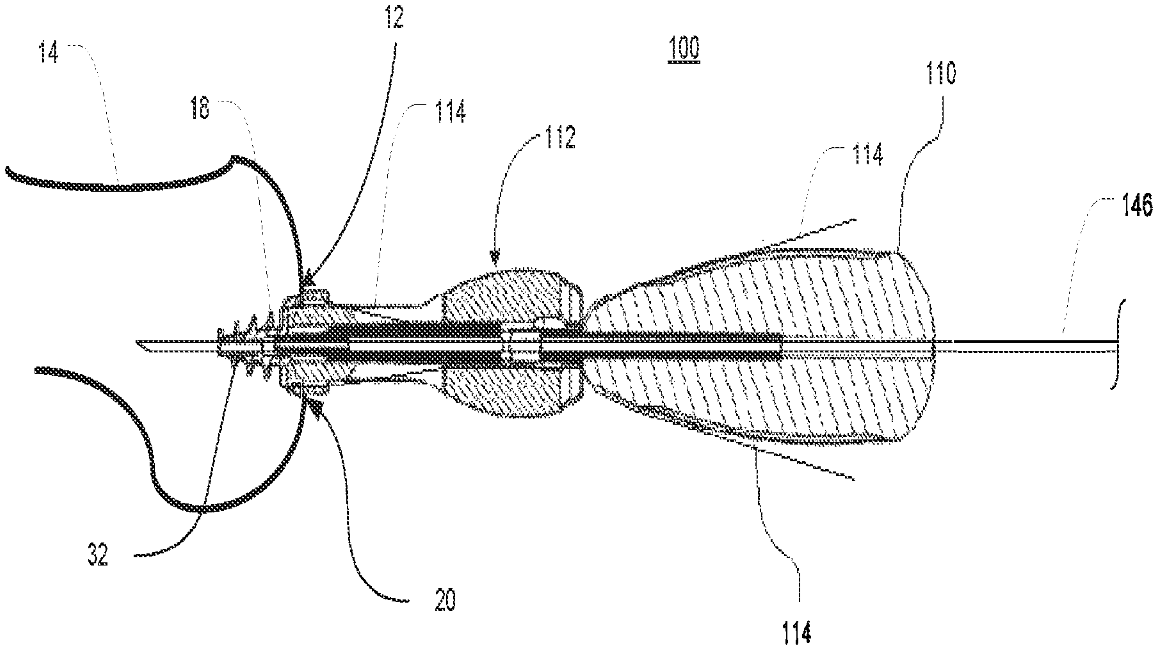
Figure 13:
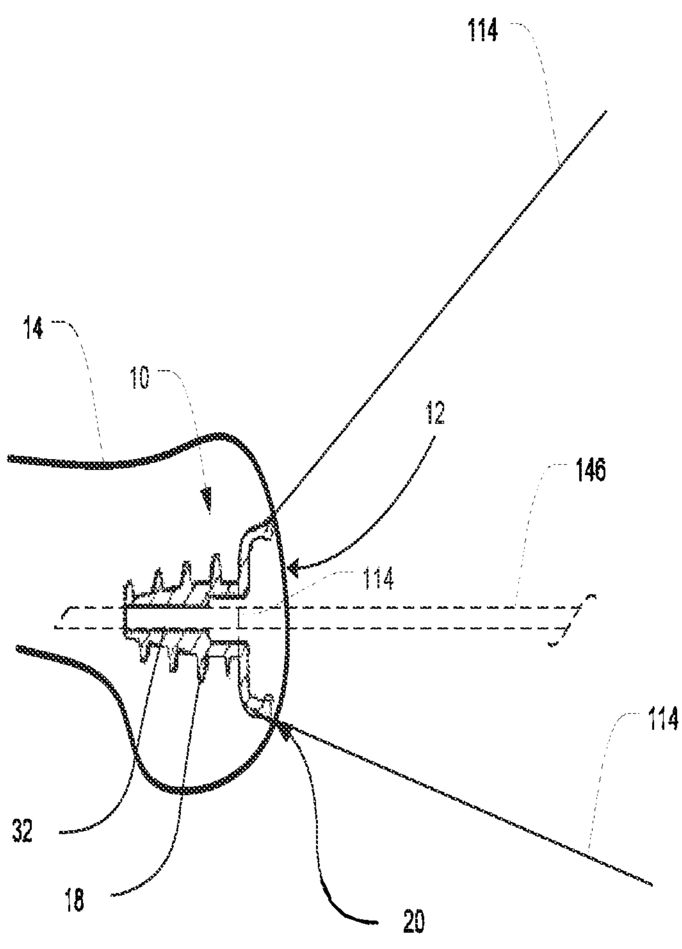
FIG. 13 generally illustrates an anchor secured in the bone consistent with at least one embodiment of the present disclosure.

With reference to FIGS. 9-13, one embodiment of system and method for using the implant delivery system 100 to secure the anchor 18 to bone within an excision site is generally illustrated. The implant delivery system 100 may include a driver 110, a biasing body 112, and at least one suture 114. As explained herein, the implant delivery system 100 may be configured to retain the anchor 18 into engagement with the driver 110 and to secure the anchor 18 to bone 14 within an excision site 20 (as generally illustrated in FIGS. 12 and 13). For example, the driver 110 may be received through the biasing body 112, and the suture 114 may be disposed around a portion of the anchor 18 to provide increased control and/or maintain contact between the driver 110 and the anchor 18 while securing the anchor 18 into the bone 14 within the excision site 20. The excision site 20 may be formed using any method and system known to those skilled in the art.

Figure 9A:
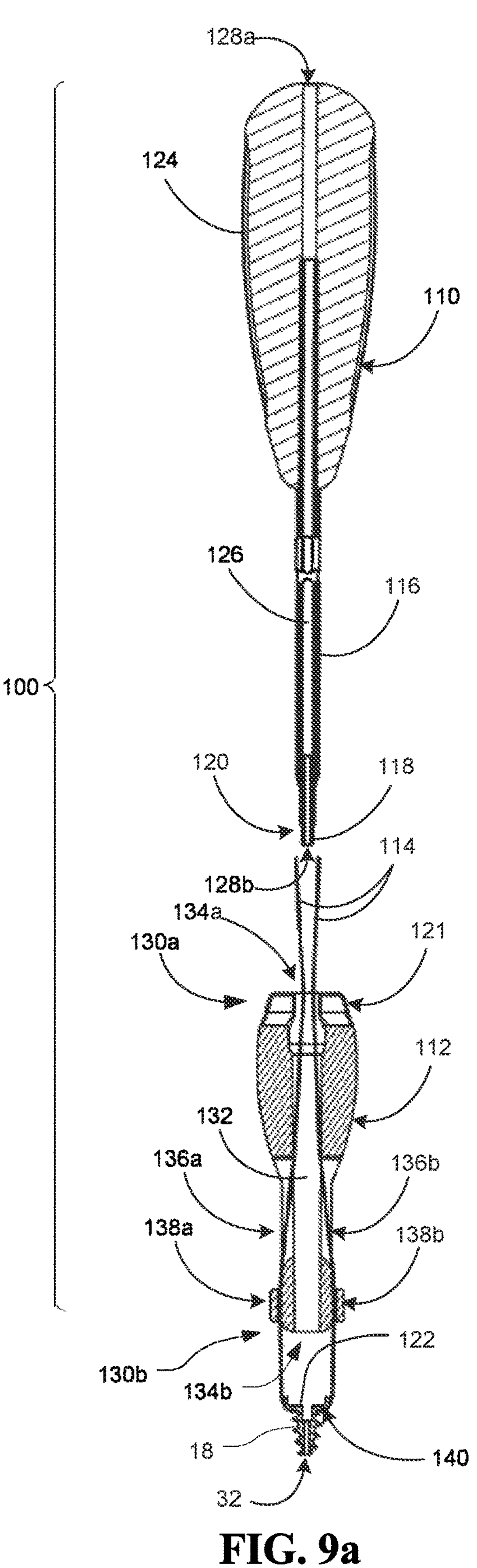
FIG. 9A generally illustrates one embodiment of an implant delivery system which may be used with the total joint replacement system consistent with at least one embodiment of the present disclosure.
Figure 9B:
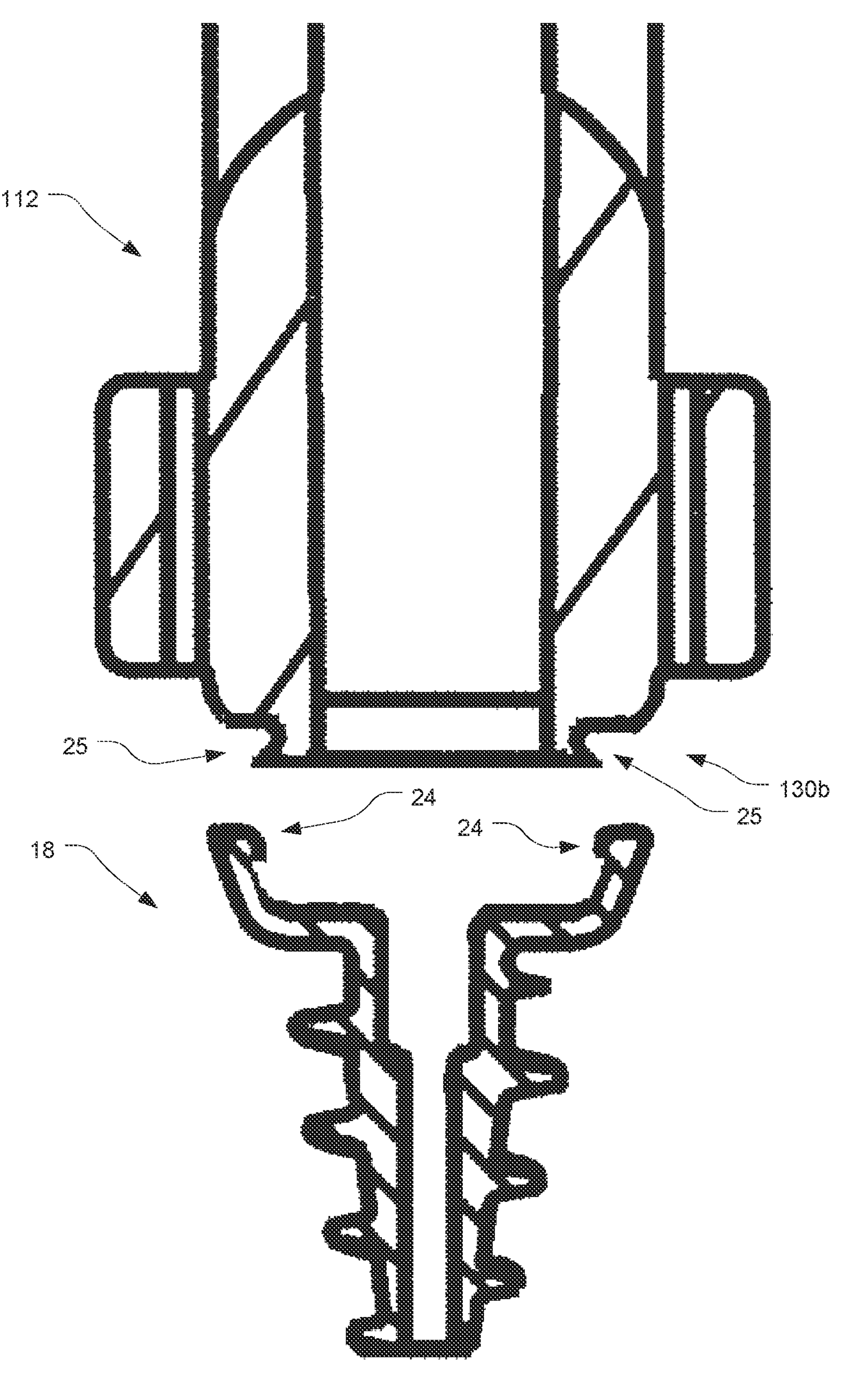
FIG. 9B generally illustrates a close up region of the implant delivery system of FIG. 9A.

The driver 110, FIG. 9A, includes a longitudinally disposed shaft 116 having an engagement portion 118 disposed about a distal end 120. The engagement portion 118 is configured to be coupled with a corresponding engagement portion 122 of the anchor 18 and to transmit torque as generally illustrated in FIGS. 10-12. For example, the engagement portion 118 may be a male-shaped coupling unit (such as, but not limited to, a splined or hex-shaped driver) configured to couple with a female-shaped coupling unit 122 (such as, but not limited to, a splined or hex-shaped recession formed in the anchor 18) in order to rotate or drive the anchor 18 into the bone. However, the engagement portions 118, 122 may vary and are not limited thereto. For example, the driver 110 may be configured to accept interchangeable bits having a different engagement portion 118 configurations, thereby allowing the engagement portion 118 of the driver 110 to be coupled to the engaging portion 122 of the anchor 18 using several different bits as necessary. Alternatively (or additionally), the engagement portion 118 may have a female-shaped coupling unit and the anchor 18 may have a male-shaped coupling unit. The shape of the engaging portions 118, 122 may be other than splined or hexagonal, and those in the art will recognize that one of any number of shapes or configuration for such components may be employed in a device or method consistent with example embodiments. Optionally, the engagement portion 118 may be magnetized or otherwise configured to maintain contact or control over the anchor 18.

While the engaging portion 122 of the anchor 18 is shown located on an inner wall of the narrow portion of the anchor 18, example embodiments may vary and are not limited thereto. For example, the engaging portion 122 of the anchor 18 may be located on an inner wall of the wide portion of the anchor 18 and/or on an outer wall of either the narrow portion or the wide portion of the anchor 18. Optionally, an intermediate or adapting portion (not shown) may be used to connect the driver 110 to the anchor 18.

The driver 110 may optionally include a handle 124. The handle 124 may facilitate grasping of the driver 110 and may be configured to cause a rotational force or a torque on the shaft 116, which may ultimately impart a rotational force or torque on the anchor 18 to secure the anchor 18 into the bone. The handle 124 may be separate from the shaft 116 (either permanently or removably coupled thereto), or may be a unitary, single piece with the shaft 116. While the handle 124 is illustrated as having a larger width than the shaft 116, example embodiments may vary and are not limited thereto. For example, the handle 124 may include a lever arm or may be configured to couple to a lever arm that is used to create the rotational force or torque.

The handle 124 and/or the shaft 116 may be cannulated to define a longitudinal passageway 126. The longitudinal passageway 126 may include proximal and distal openings 128*a*, 128*b* configured to be advanced over a guide wire (not shown for clarity), for example, when securing the anchor 18 into the bone within the excision site.

The biasing body 112 defines a shaft passageway 132 extending between a first and a second end region 130*a*, 130*b* having a first and second opening 134*a*, 134*b*. The shaft passageway 132 is configured to receive at least a portion of the shaft 116 of the driver 110, for example, as generally illustrated in FIGS. 10 and 11. The shaft 116 and the shaft passageway 132 may be configured such that the distal end 120 of the shaft 116 extends beyond the second end 134*b* of the shaft passageway 132 to allow the engagement portion 118 of the driver 110 to engage the corresponding engagement portion 122 of the anchor 18, for example, as generally illustrated in FIGS. 10 and 11. Optionally, the biasing body 112 may include a driver cradle 121, discussed in greater detail herein, which may be used to secure the implant 16 (not shown) with the anchor 18.

Additionally, the second end region 1306 may include a fixation element 25 (FIG. 9B) which substantially corresponds to the first fixation element 24 of the implant 16. In this manner, the fixation element 25 of the second end region 130*b* of the biasing body 112 may be coupled to the second fixation element 26 of the anchor 18 to generally secure the anchor 18 to the biasing body 112. The connection between the biasing body 112 and the anchor 18 may facilitate placement of the anchor 18 within the excision site by creating a generally secure connection therebetween. It may be appreciated, however, that the connection between the fixation element 25 of the second end region 130*b* and the second fixation element 26 of the anchor 18 does not need to be as strong as the connection between the first and second fixation elements 24, 26 since it is only generally intended to help advance the anchor 18 to and align the anchor 18 within the excision site.

Alternatively (or in addition to), the biasing body 112, FIG. 9A, may be configured to receive a suture 114 disposed around (e.g., wrap around) a portion of the anchor 18.

Tension may be applied to the suture 114 to generally urge the anchor 18 into contact with the driver 110 and/or the biasing body 112 to provide more control over and/or maintain contact between the driver 110 and the anchor 18. The suture 114 may be configured to extend through and/or around the biasing body 112 in any manner known to those skilled in the art. For example, the suture 114 may extend through the first opening 134*a* of the shaft passageway 132 of the biasing body 112, out through one or more suture apertures/openings/passageways 136*a*, 136*b*, through one or more suture alignment guides 138*a*, 138*b* and around a contact portion 140 of the anchor 18. The suture passageways 136*a*, 136*b* may allow the suture 114 to pass from the exterior of the biasing body 112 to the interior of the shaft passageway 132. While the suture passageways 136*a*, 136*b* are illustrated in the middle of the biasing body 112, example embodiments may vary and are not limited thereto. It should also be appreciated that the suture 114 does not have to pass through the shaft passageway 132, and instead the biasing body 112 may include one or more separate passageways (not shown) for the suture 114.

The suture alignment guides 138*a*, 138*b* are configured to retain the suture 114 about the distal end of the biasing body 112. According to one embodiment, the suture 114 may include a first and a second portion 142*a*, 142*b* (best seen in FIG. 11) which form a basket, cradle, or frame 144 extending about the contact portion of the anchor 18. The first and second portions 142*a*, 142*b* may be formed from two or more pieces of suture, or may be formed from a single piece of suture. The suture alignment guides 138*a*, 138*b* may be configured to prevent the first and second portions 142*a*, 142*b* of the cradle 144 from shipping off the anchor 18 by restricting the separation angle S of the first and second portions 142*a*, 142*b* of the cradle 144.

While the suture alignment guides 138*a*, 138*b* are shown at the distal end of the biasing body 112 nearest the anchor 18, example embodiments may vary and are not limited thereto. For example, the suture alignment guides 138*a*, 138*b* may be located anywhere along the biasing body 112 provided the suture alignment guides 138*a*, 138*b* may prevent the suture 114 from slipping off the anchor 18. Additionally, while the suture alignment guides 138*a*, 138*b* are shown as an exterior protrusion of the biasing body 112 with holes to allow the suture 114 to pass through, example embodiments may vary and are not limited thereto. For example, the suture alignment guides 138*a*, 138*b* may be flush with the biasing body 112 or may protrude in an arc shape, with a gap between one edge of the suture alignment guides 138*a*, 138*b* and the biasing body 112 to allow the suture 114 to enter. It may also be appreciated that the length of the suture alignment guides 138*a*, 138*b* may vary and the suture alignment guides 138*a*, 138*b* may be integrated into the suture passageways 136*a*, 136*b*.

While the contact portion 140 of the anchor 18 is shown on the bottom edge of the anchor 18, example embodiments may vary and the contact portion 140 may be situated anywhere along the anchor 18. For example, the contact portion 140 may also be disposed about the top portion of anchor 18. The contact portion 140 of the anchor 18 may include a flat edge or may include guides, grooves, slots, or channels configured to receive the suture 114. For example, the suture 114 may extend through a passageway formed in the anchor 18 such that a portion of the anchor 18 generally surrounds the Suture 114, and the cradle 144 may be eliminated.

To secure the anchor 18 to the bone 14 within the excision site 20, the suture 114 may be received through the biasing body 112 (e.g., through the first opening 134*a* of the shaft passageway 132, out through the suture passageways 136*a*, 136*b*, and through the suture alignment guides 138*a*, 138*b*) such that the cradle 144 is disposed about the contact portion 140 of the anchor 18 as generally illustrated in FIG. 9A. The driver 110 may be advanced through shaft passageway 132 until the engagement portion 118 contacts the corresponding engagement portion 122 of the anchor 18. The suture 114 may then be tensioned to retain the engagement between the driver 110 and the anchor 18, for example, by applying a force against the suture 114 in a direction generally away from the anchor 18 as generally illustrated in FIGS. 10 and 11. Alternatively (or in addition), the fixation element 25 (FIG. 9B) of the biasing body 112 may be secured to the fixation element 26 of the anchor 18, and the driver 110 may engage the anchor 18 as described herein.

With the anchor 18 securely engaged with the driver 110, the anchor 18 may be advanced to and aligned with the excision site 20 (as generally illustrated in FIG. 12) formed in the patient's articular surface 12 and bone 14. Optionally, the anchor 18 may be aligned with the excision site 20 using a guide wire 146 extending outwardly from the bone 14 within the excision site 20. Because the anchor 18 is retained against the driver 110, it is easier for the surgeon to align the anchor 18 relative to the excision site 20. As discussed herein, the anchor 18 may optionally include a cannulated passageway 32 (best seen in FIG. 9A) that is generally aligned with (e.g., generally co-axial) the longitudinal passageway 126 of the driver 110 (as best illustrated in FIG. 12) such that the anchor 18 and the driver 110 (and optionally the biasing device 112) may be advanced over the guide wire 146. The optionally use of the cannulated passageway 32 and the guide wire 146 may further aid in aligning the anchor 18 at the desired angle with respect to the excision site 20 and the surrounding articular surface 12.

Once the anchor 18 is aligned with respect to the excision site 20, the driver 110 may then be used to secure the anchor 18 into the bone 14, for example, by rotating the driver 110, thereby causing the anchor 18 to rotate. The height of the anchor 18 may be verified using a trial gauge (not shown) which may be easily inserted/placed into the anchor 18 to ensure that the implant 16 (e.g., FIG. 1) is substantially flush with the surrounding articular surface 21. Once the height of the anchor 18 is verified, the driver 110 (and optionally the biasing device 112 and/or the guide wire 146) may be removed, leaving the anchor 18 (and optionally the suture 114) remaining in the bone 14, as generally illustrated in FIG. 13. While the anchor 18 is illustrated having threads 21, if may be appreciated that the anchor 18 may be secured to the bone 14 using any device(s) known to those skill in the art including, but not limited to, ribs, barbs, bone cement, porous structures, and the like.

It should also be appreciated that the biasing device 112 does not have to be used when advancing and/or aligning the anchor 18 with respect the excision site 20. For example, the biasing device 112 may be eliminated and tension may be applied to the suture 114 to keep the anchor 18 engaged with the driver 110. Alternatively, the anchor 18 may be advanced to and aligned with the excision site 20 without using the driver 110. For example, the suture 114 may be secured about a portion of the anchor 18, and once the anchor 18 is aligned within the excision site 20, the driver 110 may engage the anchor 18 and used to secure the anchor 18 within the excision site 20 in the bone 14.

Turning now to FIGS. 14-17, systems and methods for securing an implant 16 to the anchor 18 using an implant delivery system 100 consistent with the present disclosure are generally illustrated. As discussed herein, the implant delivery system 100 may be configured to generate a biasing force to secure the implant 16 to the anchor 18 wherein the biasing force is only applied against the implant 16 and the anchor 18, and not the surrounding bone or tissue 14.

Figure 14:
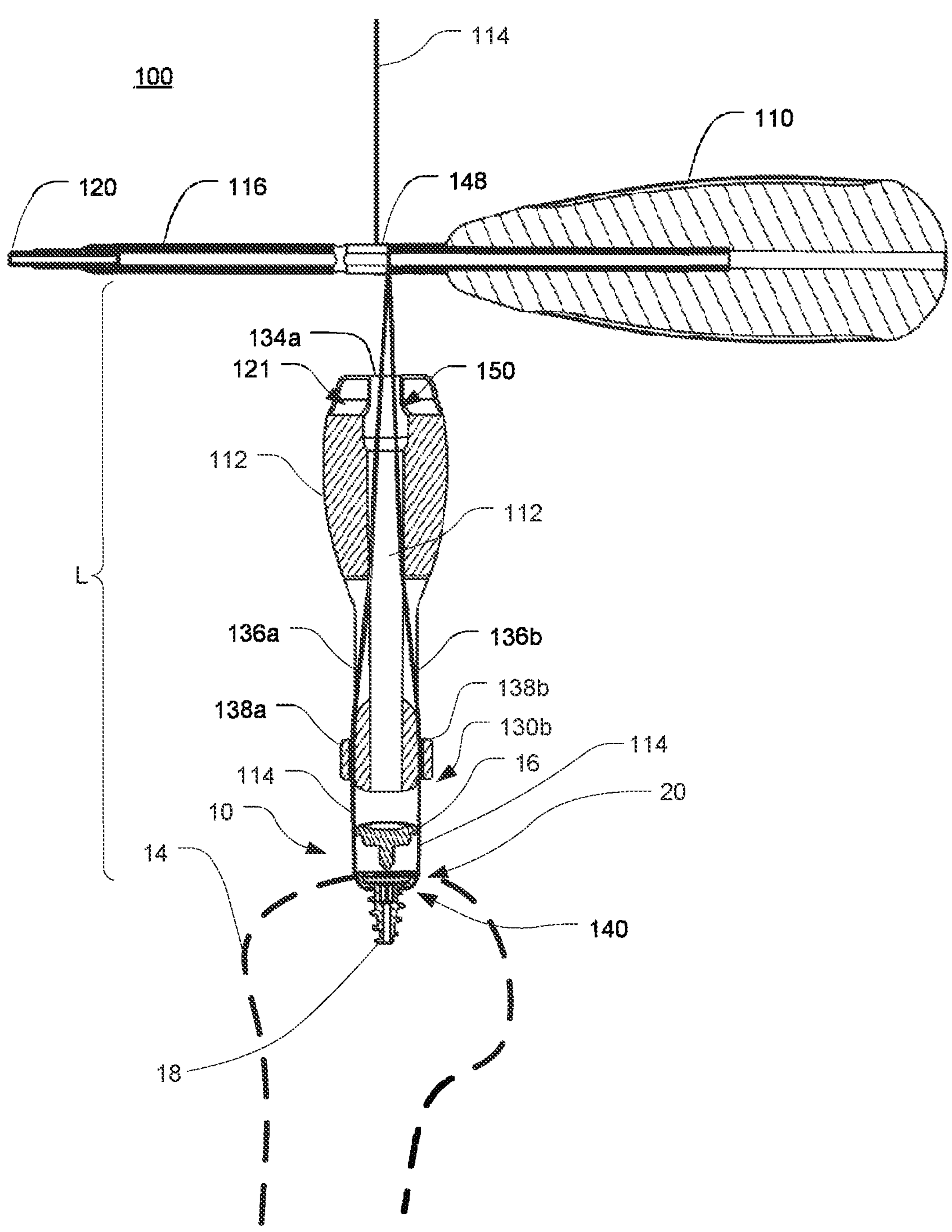
FIGS. 14-17 generally illustrate various steps in the installation/coupling of the implant with an anchor consistent with at least one embodiment of the present disclosure.
Figure 15:
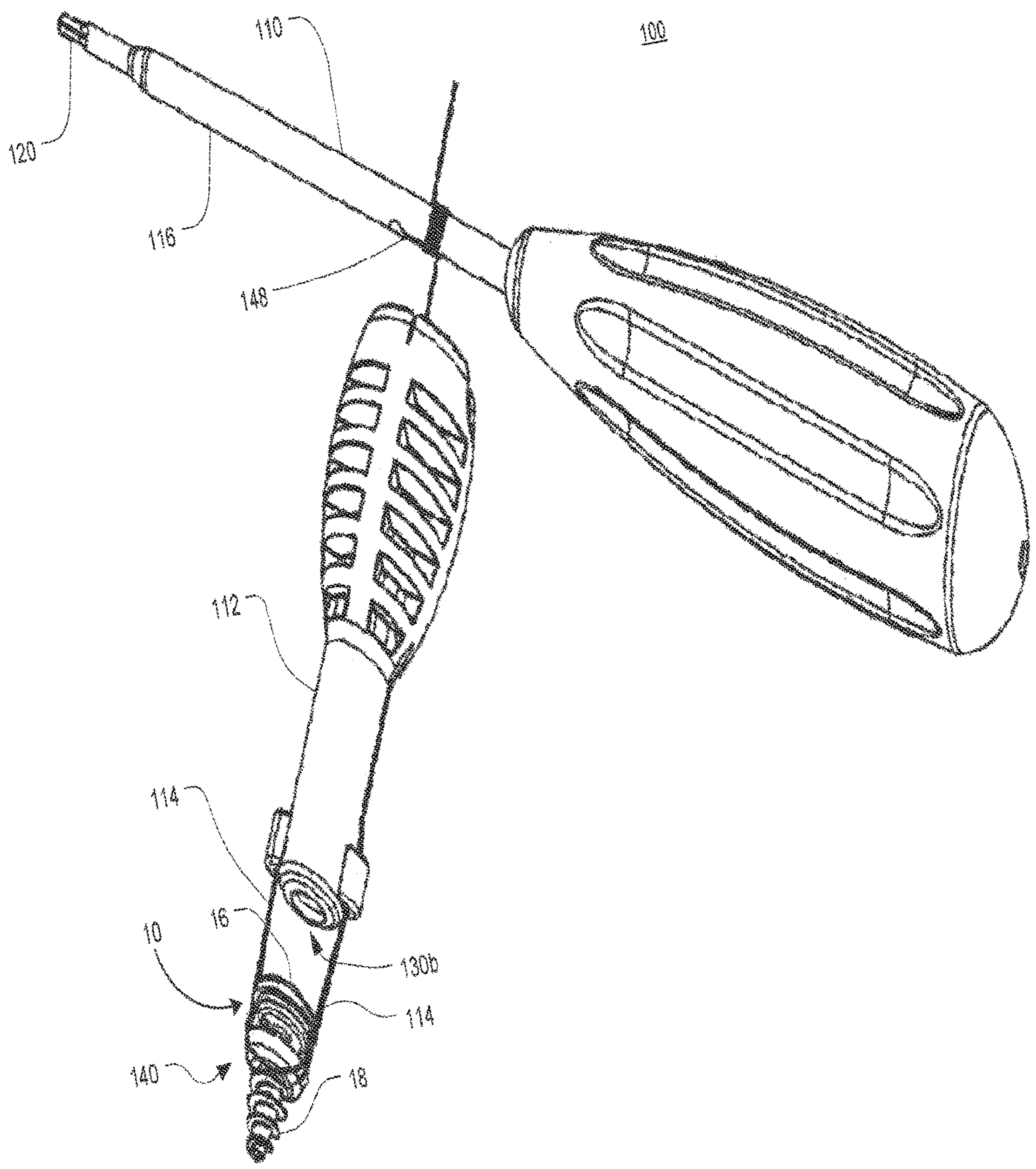

With the anchor 18 secured to the bone 14 and the suture 114 disposed about the contact portion 140 of the anchor 18 as described herein, the implant 16 may be arranged (i.e., placed) between the anchor 18 and the second end region 130*b* of the biasing device 112 as generally illustrated in FIGS. 14 and 15. The suture 114 may extend around the contact portion 140 of the anchor 18, through suture alignment guides 138*a*, 138*b* and suture passageways 136*a*, 136*b*, and exit through the first opening 134*a* of the shaft passageway 132 of the biasing body 112. The suture 114 may also be generally coupled or secured to a portion of the driver 110, for example, a portion of the shaft 116. For example, the driver 110 may include a suture engagement 148 configured to allow the suture 114 to be generally fixed or retained by the driver 130.

According to one embodiment, the suture engagement 148 may include a hole or aperture through the shaft 116. At least a portion of the suture 114 may pass through the hole 148, and the suture 114 may be secured within the suture engagement 148 as the driver 110 is rotated to reduce the length L of the suture 114 between the driver 110 and the anchor 18 as explained herein. It should be appreciated that the suture engagement 148 may include any device for generally securing the suture 114 to the driver 110. For example, the suture engagement 148 may include an external protrusion, a groove, non-cylindrical region, and/or a slot configured to secure the suture 114. Alternatively, the suture 114 may be wrapped around the shaft 116, and the tension generated by the rotation of the driver 110 may secure the suture 114 thereto. The length of the biasing body 112 may be selected to allow the surgeon sufficient room to rotate the driver 110, and therefore may depend on the intended application.

With the suture 114 generally secured to the driver 110, the driver 110 may be rotated about its longitudinal axis A as it is received within the driver cradle 121. The driver cradle 121 may be configured to receive the driver 110 (e.g., the shaft 116) and generally retain the shaft 116 as the shaft 116 is rotated relative to the biasing body 112. For example, the driver cradle 121 may include one or ore recesses, grooves, or lips formed in the first end region 134*a* of the biasing body 112. The driver cradle 121 may also include one or more holes or passageways formed through the biasing body 112 configured to receive and generally retain the shaft 116.

Optionally, the driver cradle 121 may include an enlarged opening 150 (best seen in FIG. 9). As the driver 110 is rotated, the suture 114 begins to wrap around the shaft 116, thereby increasing the diameter of the shaft 116. The enlarged opening 150 provides a void space that the suture 114 can pass through as the driver 110 is rotated and the suture 114 builds up around the shaft 116. As a result, the suture 114 may generally avoid contact with the driver cradle 121, and the torque necessary to rotate the driver 110 may be reduced.

Figure 16:
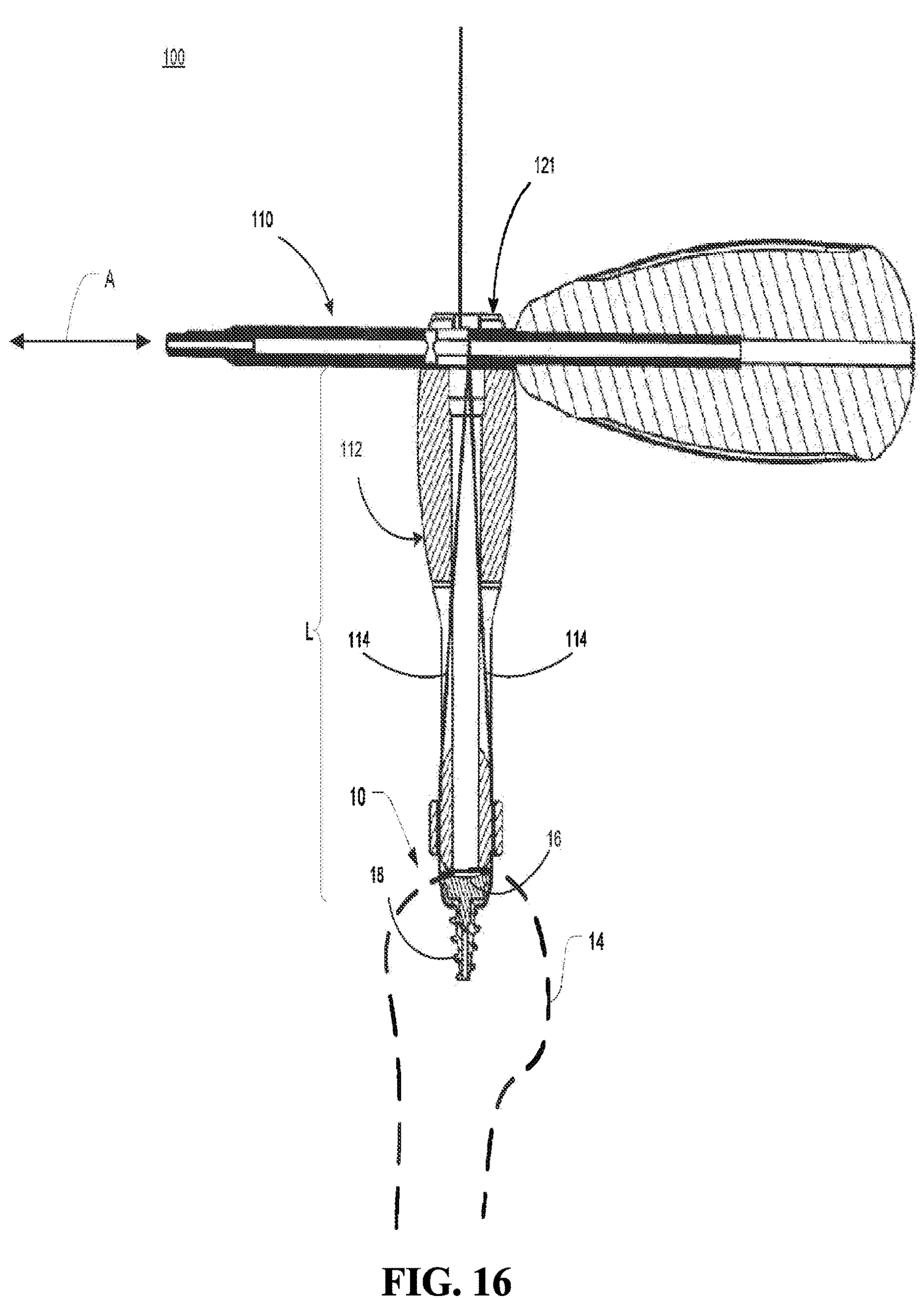
Figure 17:
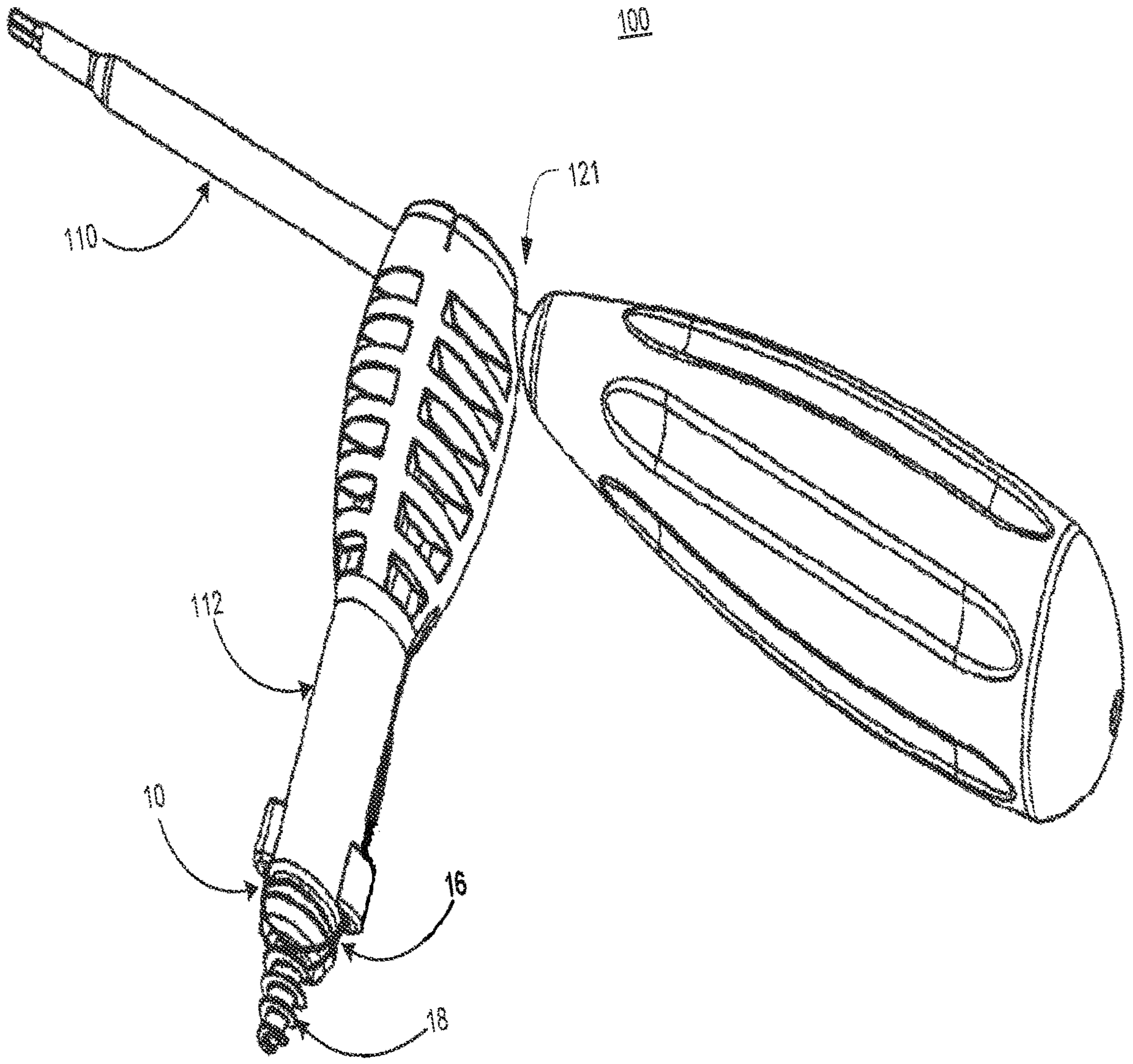

Turning now to FIGS. 16 and 17, with the implant 16 disposed between the anchor 18 and the second end region 132*b* of the biasing body 112, and the driver 110 (along with the suture 114 generally secured thereto) disposed within the driver cradle 121, the surgeon may rotate the driver 110 about longitudinal axis A to reduce the length L of the suture 114 extending between the driver 110 and the contact portion 120 of the anchor 118. The reduction in the length L of the suture 114 generates a biasing force which urges the implant 16 into engagement with the anchor 18. As may be appreciated, the implant delivery system 100 generates a biasing force which is applied against the implant 16 and anchor 18 through the suture 114 only (i.e., substantially no force is applied to the surrounding bone 14 or tissue).

More specifically, because the suture 114 supports the anchor 18, rotation of the driver 110 about longitudinal axis A increases the tension on the suture 114 (and therefore the biasing force between the implant 16 and the anchor 18) in an opposite direction of the downward force being placed upon the implant 16 by the biasing body 112. Continued rotation of the driver 110 increases the biasing force between the implant 16 and the anchor 18 and, once the biasing force exceeds the required threshold to install the implant 16, the implant 16 may be successfully installed (e.g., secured) in the anchor 18. Thus, as a result of the suture 114 applying a relatively equal and opposite force to the anchor 18 and the biasing device 110 (and therefore the implant 16), the underlying bone 14 and other structures are not affected, preventing or reducing potential injury from securing the implant 16 into the anchor 18. The implant delivery system 100 therefore avoids and/or reduces any impact to the bone 14 (e.g., eliminates blunt force due to a hammer/mallet or the like), and therefore avoids and/or reduces damage to the bone 16.

Because the biasing force is not transmitted/applied into the surrounding bone 14 of tissue, the implant delivery system 100 may be used with small bones (such as, but not limited to, phalange bones and/or metatarsal bones in the foot and/or hands. Additionally, because the implant delivery system 100 is capable of generating high biasing forces without transmitting/applying the biasing force to the surrounding bone 14 or tissue, the connection between the implant body 16 and the anchor 18 (e.g., first and second fixation elements 24, 26 as discussed herein) may be stronger and more robust, thereby increasing the life expectancy of the implant system 10. Moreover, the implant delivery system 100 may deliver the biasing force uniformly to the implant 16 and be self-leveling or self-aligning, thereby reducing and/or eliminating the difficulties associated with aligning the implant 16 with respect to the anchor 18.

Once the implant 16 is secured to the anchor 18, the suture 114 may be removed from the implant system 10. For example, one or more portions of the suture 114 may be cut and the resulting pieces may be removed (e.g., pulled out) from the excision site 20. Alternatively, a first end of the suture 114 may be released and the suture 114 may be pulled through the biasing body 120 by a second end of the suture 114, resulting in the first end traveling through the shaft passageway 132*c*, through one of the suture passageways 136*a*, 136*b*, out one of the alignment guides 138*a*, 138*b*, around the anchor 18 and through the second of the alignment guides 138*a*, 138*b* and suture passageways 136*a*, 136*b*, and the shaft passageway 132. However, example embodiments may vary and are not limited thereto.

If the suture 114 is cut prior to removal, example embodiments may vary and may include the suture 114 having various shapes or loops. For example, the suture 114 may form a basket or loop to wrap around the anchor 18. This shape may help support the anchor 18 and may increase control over the anchor 18 prior to the suture 114 being wrapped around the driver 110. In this configuration, the loop may extend so that the loop can be severed after installation of the implant system 10.

It may be appreciated that the strength or ruggedness of the snap-fit connection between the implant 16 and the anchor 18 may depend on the selected materials (e.g., the rigidity) and size/dimensions. In general, more rigid (i.e., less deformable) materials and/or larger sizes/dimensions will result in a stronger, more robust connection between the implant 16 and the anchor 18. While a stronger and more robust connection between the implant 16 and the anchor 18 is generally desirable, the resulting force necessary to make the snap-fit connection increases.

Traditionally, the force necessary to secure the implant 16 to the anchor 18 has been generated using a blunt force, e.g., a hammer/mallet or the like. More specifically, with the anchor 18 secured in the bone 14, the surgeon attempts to align the implant 16 relative to the anchor 18 and impacts the implant 16 with the hammer/mallet to force the implant 16 into engagement with the anchor 18. As may be appreciated, however, a substantial amount of force is also applied to the surrounding bone 14, and if the force applied to the bone 14 is too great, the bone 14 may be damaged. Consequently, the strength of the connection between the implant 16 and the anchor 18 may be limited in many applications (e.g., but not limited to, small bones in the hand and foot as well as implant system 10 installed proximate to the perimeter of a bone) by the strength of the surrounding bone 14. Additionally, it may be very difficult for the surgeon to properly align the implant 16 with respect to the anchor 18.

As discussed herein, the implant delivery system consistent with one embodiment of the present disclosure solves this problem by generating a biasing force to secure the implant 16 to the anchor 18 wherein the biasing force is only applied against the implant 16 and the anchor 18. The biasing force generated by the implant delivery system may therefore be applied only to the implant system 10, and not the surrounding bone or tissue 14. An implant delivery system consistent with the present disclosure may also be used to facilitate securing the anchor 18 into the bone 14.

It should be appreciated that the implant system 10 illustrated with respect to FIGS. 9-17 is provided for illustrative purposes, and that the implant delivery system may be used with any multi-piece implant having an anchor that is coupled (either directly or indirectly) to an implant/implant body. For example, the implant delivery system may be used with implant systems for replacing any articular surface such as, but not limited to, shoulder joints (e.g., but not limited to, the glenohumeral joint), hip joint (e.g., but not limited to, the acetabulofemoral joint), foot and/or hand joints (e.g., but not limited to, metacarpophalangeal joints, metatarsophalangeal joints, and/or interphalangeal joints), or the like. The implant systems may include total joint implants (wherein all or substantially all of the articular surface of at least one bone is replaced with the artificial surface of the implant) and/or partial implants (wherein substantially only the damaged portion(s) of the articular surface of a bone is replaced with the artificial surface of the implant). The implant delivery system may also be used to secure together a multi-piece pin or rod in a bone to facilitate healing of a fracture or broken bone.

Figure 18:
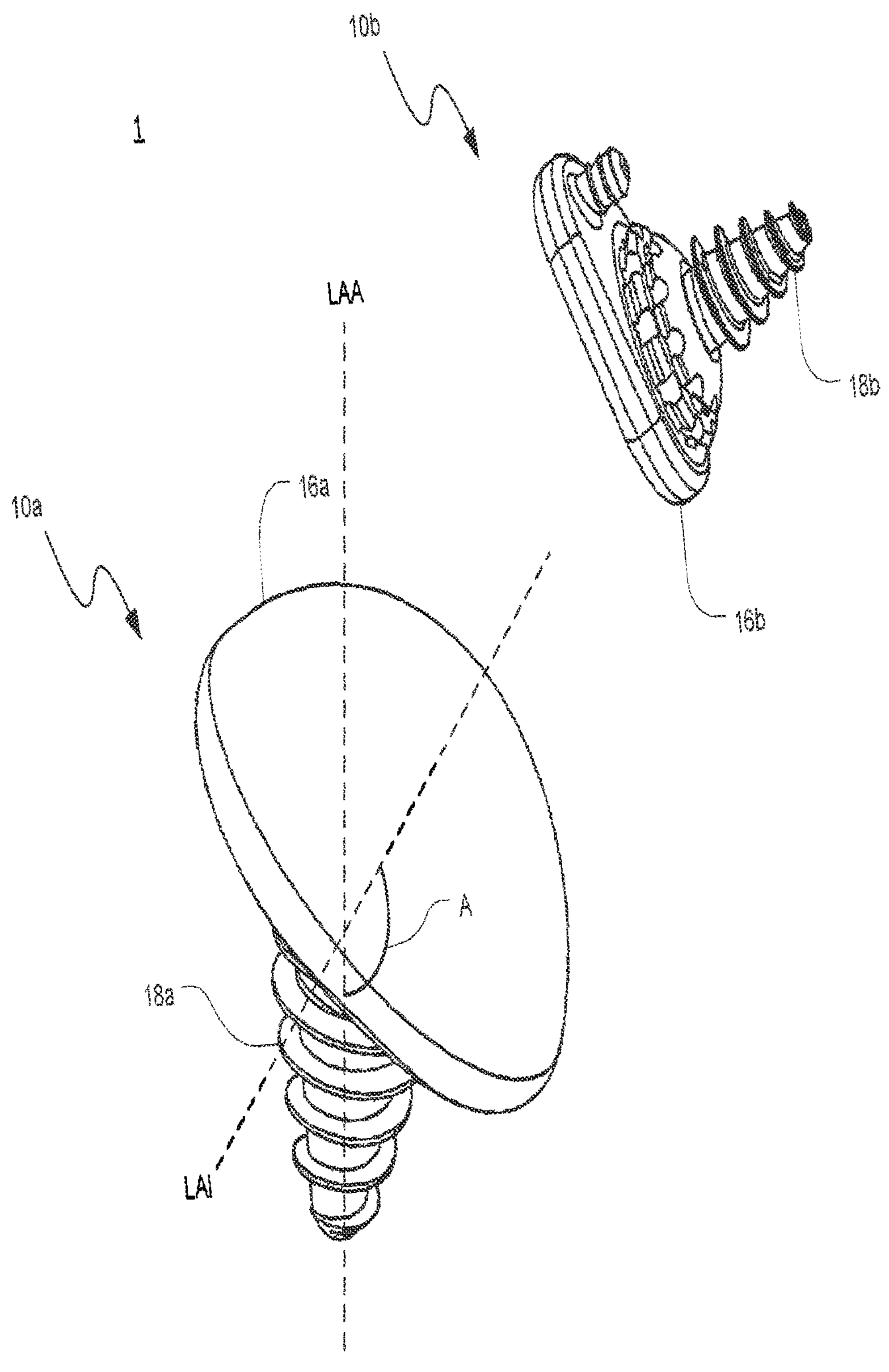
FIG. 18 generally illustrates yet another embodiment of an implant system which may be used with the total joint replacement system consistent with at least one embodiment of the present disclosures.

Turning now to FIG. 18, yet another embodiment of the total joint replacement system 1 consistent with the present disclosure is generally illustrated. The total joint replacement system 1 may include first implant system 10*a* and a second implant system 106. While the total joint replacement system 1 will be described in terms of a shoulder joint, it should be appreciated that this is not a limitation of the present disclosure unless specifically claimed as such. For the sake of clarity, the bones are not illustrated.

The first implant system 10*a* may be configured to replace and/or repair the humeral head, and may be similar to the implant system 10 described with respect to FIGS. 4 and 5-6. The implant 16*a* may include a first fixation element 32 configured to be secured to the second fixation element 44 of the anchor 18*a* as described herein (e.g., using one or more first fixation elements 32 configured to be secured to one or more second fixation elements 44). The anchor 18*a* may be secured, for example, into the humerus. The implant 16*a* may have a generally hemispherical configuration, for example, which generally corresponds to the humeral head (e.g., a "ball shape"). The implant 16*a* (e.g., the first fixation element 32) may be configured to be secured to the anchor 18*a* (e.g., the second fixation element 44) at any angle A. For example, the angle A may be defined by the longitudinal axis LAA of the anchor 18*a* and the longitudinal axis LAI of the implant 16*a*. The angle A may be determined based on the amount of the humeral head removed with respect to the rest of the humerus. The angle A may include any angle within the range of 0 degrees to approximately 90 degrees, for example, within the range of 0 degrees to approximately 45 degrees, within the range of 0 degrees to approximately 25 degrees, and/or within the range of 0 degrees to approximately 15 degrees, including all values and ranges therein.

The second implant system 10*b* may be configured to replace and/or repair the glenoid. The second implant system 10*b* may include any implant system/assembly as described in U.S. Provisional Application Ser. No. 61/949,789, filed Mar. 7, 2014, which is fully incorporated herein by reference.

Figure 19:
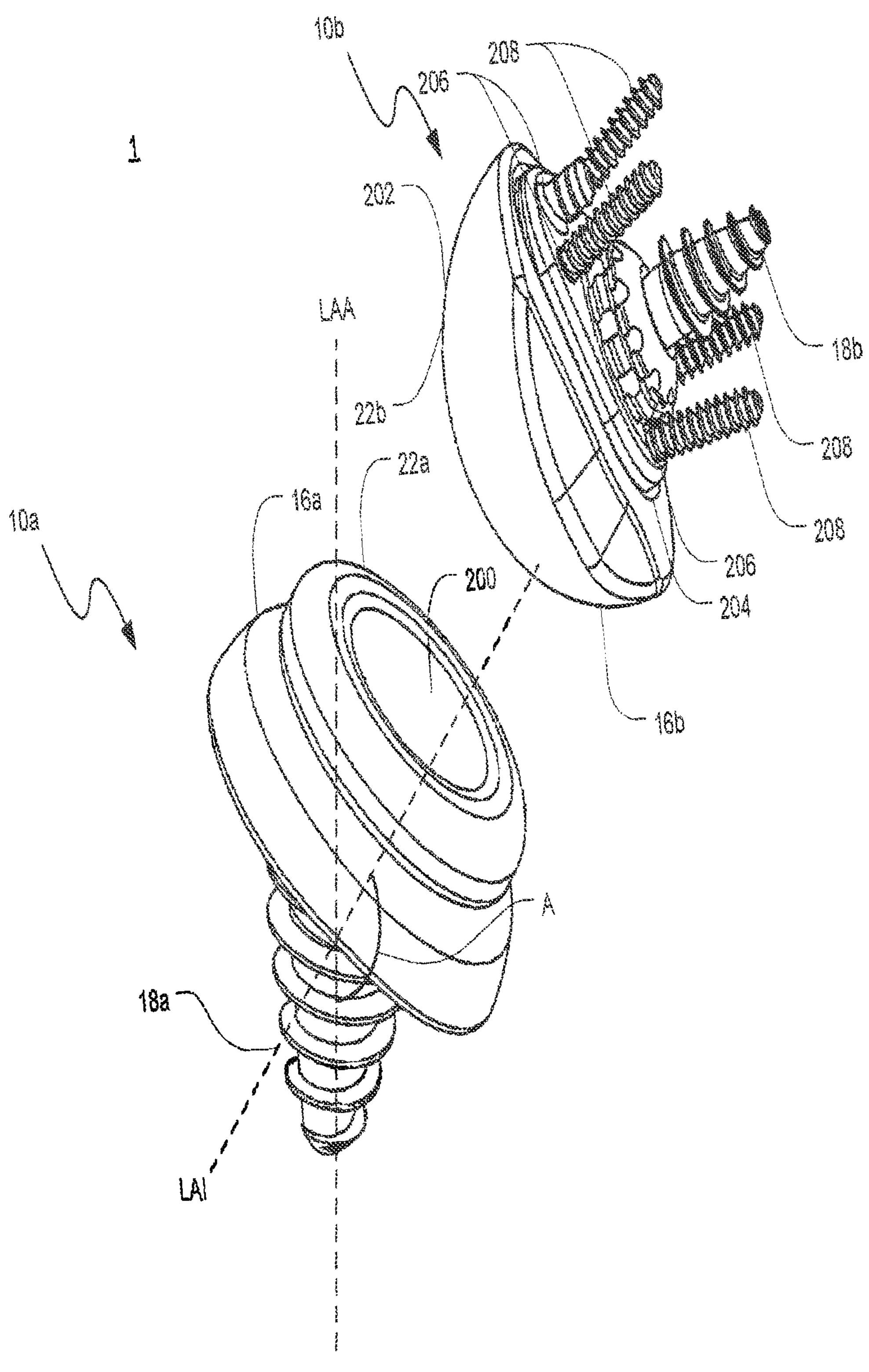
FIG. 19 generally illustrates a further embodiment of an implant system which may be used with the total joint replacement system consistent with at least one embodiment of the present disclosure.

The total joint replacement system 1 as generally illustrated in FIG. 18 may therefore repair and/or replace the shoulder joint. Turning now to FIG. 19, yet a further embodiment of the total joint replacement system 1 consistent with the present disclosure is generally illustrated. The total joint replacement system 1 of FIG. 19 may include first implant system 10*a* and a second implant system 10*b*, and may be used to repair and/or replace a shoulder joint (though it should be appreciated that this is not a limitation of the present disclosure unless specifically claimed as such). For the sake of clarity, the bones are not illustrated.

The total joint replacement system 1 may be referred to as a "reverse shoulder." The shoulder may be thought of as a ball and socket joint in which he humeral head is a ball and the glenoid is a socket. In the total joint replacement system 1 of FIG. 19, the orientation of the ball is socket is reversed. As such, implant system 10*a* (which may be secured to the humerus) may include an anchor 18*a* and an implant 16*a* having a load bearing surface 22 at least partially defining a socket 200. The implant 16*a* may be disposed at an angle A with respect to the anchor 18*a* as described herein.

The second implant system 10*b* may include an implant 16*b* and an anchor 18*b*. The implant 16*b* may be secured to the anchor 18*b* as generally described herein (e.g., using one or more first fixation elements 32 configured to be secured to one or more second fixation elements 44). The implant 16*b* may include an implant body 202 and a support plate 204. The implant body 202 may define a load bearing surface 22*b*, for example, having a generally hemi-spherical configuration (e.g., ball) configured to articulate in the socket 200 of the first implant system 10*a*. The implant body 202 may be scoured to the support plate 204 in any manner known to those skilled in the art. For example, the implant body 202 may be secured to the support plate 204 using a tapered connection similar to the first and second fixation elements 32, 44 as described herein. The support plate 204 may optionally include one or more apertures 206 configured to receive anchoring screws 208. The anchoring screws 208 aid in securing the support plate 204 (and therefore the implant 18*b*) to the bone.

According to one embodiment, the total joint replacement system 1 of FIG. 18 may be partially replaced with the total joint replacement system 1 of FIG. 19. In particular, a patient may initially have the total joint replacement system 1 of FIG. 18 installed in the shoulder joint. If it is later desired to replace the total joint replacement system 1 of FIG. 18 with a reverse shoulder, the anchors 18*a*, 18*b* of FIG. 18 may remain secured within the humerus and glenoid, respectively. The implants 16*a*, 16*b* of FIG. 18 may be removed and replaced with the implants 16*a*, 16*b* of FIG. 19. Leaving the anchors 16*a*, 16*b* of FIG. 18 within the bones reduces the potential for damage to the bones if corrective surgery is later needed. As such, any of the implants 10 that may be used with the total joint replacement system 1 of the present disclosure may be considered modular.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited of referred to in this application are incorporated in their entirety herein by reference.

What is claimed is:

1. An implant delivery system comprising:

a driver having:

i. a handle;

ii. a driver shaft extending distally from the handle and having a longitudinal passageway disposed through a longitudinal axis of the driver shaft; and iii. a driver engagement portion extending from a distal end of the driver shaft and configured to detachably couple with an anchor;

a biasing body having a biasing body passageway extending longitudinally therethrough and configured to at least partially receive the driver shaft; and a suture configured to facilitate control, maintain contact, or both, between the anchor and one or both of the driver and the biasing body;

wherein a proximal portion of the biasing body further comprises a driver cradle configured to receive at least a portion of the driver when a longitudinal axis of the driver is at a position generally perpendicular to a longitudinal axis of the biasing body.

2. The implant delivery system of claim 1, wherein the driver engagement portion is configured to be received in a receptacle disposed in an engagement portion of the anchor.

3. The implant delivery system of claim 2, further comprising an interconnect to connect the driver engagement portion to the anchor engagement portion.

4. The implant delivery system of claim 2, wherein the driver engagement portion comprises a hex-shaped configuration.

5. The implant delivery system of claim 2, wherein the driver engagement portion comprises a splined configuration.

6. The implant delivery system of claim 2, wherein the driver engagement portion is magnetic.

7. The implant delivery system of claim 2, wherein the driver engagement portion is a female-shaped coupling unit and the anchor engagement portion is male shaped.

8. The implant delivery system of claim 1, wherein the driver shaft is configured to detachably couple with a plurality of engagement portions of the anchor having different geometries.

9. The implant delivery system of claim 1, wherein the handle is cannulated such that the longitudinal passageway extends from the driver shaft therethrough.

10. The implant delivery system of claim 9, wherein the driver is configured to be advanced over a guide wire such that the guide wire passes through the longitudinal passageway.

11. The implant delivery system of claim 1, wherein the biasing body further comprises a fixation element configured to detachably couple with an implant.

12. An implant delivery system comprising:

a driver comprising:

i. a handle;

ii. a shaft extending distally from the handle; and iii. a driver engagement portion extending from a distal end of the shaft and configured to detachably couple with an anchor; and a biasing body comprising:

i. a biasing body passageway extending through a longitudinal axis of the biasing body and configured to at least partially receive the driver;

ii. one or more suture passageways disposed through an outer surface of the biasing body and into the biasing body passageway, wherein each suture passageway is configured to allow a suture to pass from the exterior of the biasing body through to the biasing body passageway; and iii. one or more suture alignment guides fixedly attached to the biasing body and configured to:

a.) retain the suture about a distal portion of the biasing body;

b.) provide alignment between the suture and a contact portion of the anchor; or c.) both retain the suture about the distal portion of the biasing body and provide alignment between the suture and the contact portion of the anchor; and the suture configured to facilitate control, maintain contact, or both, between the anchor and one or both of the driver and the biasing body.

13. The system of claim 12, wherein the one or more suture alignment guides extend radially from the outer surface of the biasing body.

14. The system of claim 13, wherein the one or more suture alignment guides extend radially from the outer surface of the biasing body to form an arc shape comprising a gap located between an outer surface of the arc shape and the outer surface of the biasing body such that the gap is configured to allow the suture to pass therethrough.

15. The system of claim 12, wherein the one or more suture alignment guides are at least partially flush with the outer surface of the biasing body.

16. The system of claim 12, further comprising a coupling region extending from a distal portion of the biasing body and configured to couple the biasing body with an anchor engagement portion.

17. The system of claim 12, further comprising a guide wire configured to pass through a longitudinal passageway of the driver, the biasing body passageway of the biasing body, and a bore disposed through a longitudinal axis of the anchor.

18. The system of claim 12, wherein the biasing body further comprises a driver cradle configured to interface with the driver.

19. The system of claim 18, wherein the driver cradle comprises one or more of recesses, grooves, or lips or any combination thereof.

20. The system of claim 18, wherein the driver cradle comprises one or more of holes and/or passageways formed through the biasing body and configured to generally retain the shaft of the driver.

* * * * *